United States Patent [19]
Sun et al.

[11] Patent Number: 5,962,762
[45] Date of Patent: *Oct. 5, 1999

[54] USE OF TRANSITION METAL CONTAINING SMALL PORE MOLECULAR SIEVE CATALYSTS IN OXYGENATE CONVERSION

[76] Inventors: Hsian-Ning Sun, 4212 Villanova, Houston, Tex. 77005; Stephen Neil Vaughn, 1111 Southern Hills, Kingwood, Tex. 77339

[ * ] Notice: This patent issued on a continued prosecution application filed under 37 CFR 1.53(d), and is subject to the twenty year patent term provisions of 35 U.S.C. 154(a)(2).

[21] Appl. No.: 08/571,506

[22] Filed: Dec. 13, 1995

[51] Int. Cl.⁶ .............................. C07C 1/00; C07C 1/20
[52] U.S. Cl. .................... 585/640; 585/638; 585/639; 585/642
[58] Field of Search .................... 585/638, 639, 585/640, 642

[56] References Cited

U.S. PATENT DOCUMENTS

| | | | |
|---|---|---|---|
| 4,021,332 | 5/1977 | Wilson et al. | 208/120 |
| 4,077,910 | 3/1978 | Wilson et al. | 252/455 |
| 4,292,458 | 9/1981 | Klotz | 585/469 |
| 4,311,865 | 1/1982 | Chen et al. | 585/640 |
| 4,499,327 | 2/1985 | Kaiser | 585/640 |
| 4,677,242 | 6/1987 | Kaiser | 585/638 |
| 4,677,243 | 6/1987 | Kaiser | 585/638 |
| 4,752,651 | 6/1988 | Kaiser | 585/640 |
| 4,849,575 | 7/1989 | Lewis | 585/640 |

OTHER PUBLICATIONS

Stanislaw Ceckiewicz, "Conversion of Methanol into Light Hydrocarbons on Erionite–Offretite(T) Zeolite", *J. Chem. Soc.*, Fraday Trans. 1, vol. 80, No. 11, pp. 2989–2998 (1984). No month available.

Tomoyuki Inui, et al., "Highly Selective Synthesis of Ethene from Methanol on a Novel Nickel–Silicoaluminophosphate Catalyst", *J. Chem. Soc.,* Chem. Commun., pp. 205–206 (1990). No month available.

Tomoyuki Inui, "Structure–Reactivity Relationships in Methanol to Olefin Conversion on Various Microporous Crsytalline Catalysts" *Structure–Activity and Selectivity Relationship in Heterogeneous Catalysts,* Elsevier Science Publishers B.V. Amsterdam, pp. 233–242 (1991). No month available.

Naoto Azuma, et al., "Electron Spin Resonance Study of Ni(I) in Silicoaluminophosphate Type 11: Adsorbate Interactions and Evidence for Framework Incorporation of Ni(I)" *Journal of Physical Chemistry,* vol. 98, No. 4, pp. 1217–1221 (1994). No month available.

Naoto Azuma, et al., "Electron Spin Echo Modulation Spectroscopic Evidence for Framework Substitution of Ni(I) in NiAPSO–11", *Zeolites and Related Microporous Materials: State of the Art 1994,* Studies in Surface Science and Catalysis, vol. 84, Elsevier Science B.V. (1994) No month available.

Naoto Azuma, et al., "Nickel(I) Location and Adsorbate Interactions in Nickel(II)—Exchanged Silicoaluminophosphate Type 5 As Determined by Electron Spin Resonance and Electron Spin Echo Modulation Spectroscopies", *Journal of Physical Chemistry,* vol. 99, No. 17, pp; 6670–6676 (1995). No month available.

V. Mavrodinova et al, "Effect of the Introduction of Ni(II)—On the Catalytic Properties of SAPO–5 Molecular Sieves", *Zeolite Chemistry and Catalysis,* Elsevier Science Publishers B.V. Amsterdam, pp. 295–302, (1991). No month available.

*Primary Examiner*—Elizabeth Wood
*Attorney, Agent, or Firm*—Bradley A. Keller

[57] ABSTRACT

A method for converting starting material to olefins comprising contacting the starting material with a small pore molecular sieve catalyst under effective conditions to produce olefins, wherein the molecular sieve has been modified after synthesis by incorporation of a transition metal ion using a transition metal compound, wherein the transition metal ion is selected from the group comprising Groups VIB, VIIB, or VII or mixtures thereof.

17 Claims, No Drawings

USE OF TRANSITION METAL CONTAINING SMALL PORE MOLECULAR SIEVE CATALYSTS IN OXYGENATE CONVERSION

BACKGROUND OF THE INVENTION

1. Field of Invention

This invention relates to a process for the conversion of oxygenates to hydrocarbons using small pore molecular sieve catalysts. More particularly, this invention relates to a process for conversion of oxygenates to olefins using silicoaluminophosphate molecular sieve catalysts which have been incorporated with certain transition metals after the synthesis of the molecular sieve.

2. Background Art of the Invention

Olefins have traditionally been produced through the process of petroleum cracking. Because of the potential limited availability and high cost of petroleum sources, the cost of producing olefins from such petroleum sources has been steadily increasing. Light olefins such as ethylene serve as feeds for the production of numerous chemicals.

The search for alternative materials for the production of light olefins, such as ethylene, has led to the use of oxygenates such as alcohols, and more particularly to methanol and ethanol or their derivatives as feedstocks. These and other alcohols may be produced by fermentation or from synthesis gas. Synthesis gas can be produced from natural gas, petroleum liquids, carbonaceous materials including coal, recycled plastics, municipal wastes, or any organic material. Thus, alcohol and alcohol derivatives may provide non-petroleum based routes for hydrocarbon production.

It is well known in the prior art to convert oxygenates to olefins by contacting the oxygenate with various types of catalysts. Medium and large pore molecular sieve catalysts, such as borosilicate, ZSM-5, SAPO-11, and SAPO-5, may be used. For example, U.S. Pat. No. 4,292,458 teaches a process in which a crystalline borosilicate, is converted to the hydrogen form, ion-exchanged with $Ni(NO_3)_2$ in water, washed, and then calcined to give a catalyst useful for conversion of methanol to ethylene and propylene (among other products). Similarly, U.S. Pat. No. 4,311,865 teaches the use of the medium pore zeolite, ZSM-5 (approximately 5.5 Angstroms) pore size of, which is ion-exchanged with cobalt, and then calcined to produce a catalyst which is then used to convert methanol to hydrocarbons (including olefins). Both of these processes use ion-exchange to add the metal to the medium pore molecular sieve. The following references also teach the process of using the large pore catalyst SAPO-5 (pore size of approximately 8.0 Angstroms), for conversion of methanol to olefin; however, in these instances, the nickel is incorporated during synthesis, rather than by the use of ion-exchange: N. Azuma, et al., Nickel(I) Location and Adsorbate Interactions in Nickel(II)-Exchanged Silicoaluminophosphate Type 5 As Determined by Electronic Spin Resonance and Electron Spin Echo Modual Spectroscopies, *Journal of Physical Chemistry*, Vol. 99, No. 17, pages 6670–6 (1995) and V. Mavrodinova et al., Effect of the Introduction of Ni(II)—On the Catalytic Properties of SAPO-5 Molecular Sieves, *Zeolite Chemistry and Catalysis*, Pages 295–302, Elsevier Science Publishers B. V. Amsterdam (1991).

Small pore catalysts such as SAPO-34, have been used to convert methanol to olefins, as described in an article by T. lnui, Structure-Reactivity Relationships in Methanol to Olefins Conversion in Various Microporous Crystalline Catalysts, *Structure-Activity and Selectivity Relationships in Heterogensis Catalysts*, pages 233–42, Elsevier Science Publishers B. V. Amsterdam (1991). However, the conversion stability is not as good as when using medium pore molecular sieves which have been ion-exchanged with the metals. Based on the favorable effect of metal addition to medium pore molecular sieve, it would seem that this same effect would be seen using small pore molecular sieves. However, until now, as taught by Inui, the metal ion had to be incorporated into the catalyst during synthesis, rather than by post-synthesis ion exchange.

Inui has confirmed that nickel substitution into SAPO-34 during the synthesis process results in improving the selectivity of methanol to ethylene. Inui's experiments tested three different SAPO-34 catalysts for use in the conversion process. In the first, the catalyst without any nickel substitution was used as a comparative sample. In the second and the third, nickel was substituted during the synthesis for a resulting silicon to nickel ratio of 100 and 40 respectively. In all three experiments, a feed of 20% methanol and 80% nitrogen diluent was used. The reactions were carried out at a total pressure of one atmosphere (0.1 MPa), a temperature of 450° C., and a gas hourly space velocity (GHSV) of 2,000 $hr^{-1}$.

The experiments teach that the ethylene yield will increase from 30% to 60% by using the Ni-SAPO-34 catalyst with the Si/Ni ratio of 100, as compared to the untreated SAPO-34 catalyst. Inui's use of the Ni-SAPO-34 catalyst with the Si/Ni ratio of 40 increased the ethylene yield from 30% to 90% as compared to the untreated SAPO-34 catalyst. The combined ethylene and proplyene yield was also increased on an absolute basis by 25% and 34%, respectively.

One can see that the nickel incorporation has a definite impact upon the ethylene and propylenes yields. However, even though Inui has demonstrated that nickel substitution is attractive, the nickel was substituted during the catalyst synthesis process. Metal substitution via catalyst synthesis generally requires elevated temperatures, elevated pressures, and special equipment, therefore making it commercially less attractive. In contrast, post-synthesis metal incorporation can be carried out under milder conditions. In addition, the physical characteristics, such as particle size, can be varied prior to metal incorporation to achieve greater flexibility, thus allowing a wider range of operating parameters with which to achieve the incorporation.

Therefore, in view of the problems associated with incorporating the metal during synthesis, it would be commercially useful and desirable to be able to produce such a catalyst by incorporating after molecular sieve synthesis, rather than during synthesis. A post-synthesis technique would provide flexibility in catalyst preparation, choice of metal additive, metal concentration, and selection of molecular sieves.

SUMMARY OF INVENTION

This invention provides a method for converting oxygenates to olefins, comprising contacting the starting material with a small pore molecular sieve catalyst under effective conversion conditions to provide olefins wherein the molecular sieve has been modified after synthesis by incorporation of a transition metal (from Groups VIB, VIIB, or VII as defined by the CAS Version in the CRC Handbook of Chemistry and Physics, 74th edition, 1993) originating from a metal compound.

DETAILED DESCRIPTION OF THE INVENTION

The present invention is characterized by use of a small pore molecular sieve catalyst, which has a transition metal incorporated after molecular sieve synthesis, rather than during synthesis, in a process for convating oxygenates to olefins.

For this application, the molecular sieve may be a zeolite, such as ZSM-34, a silicoaluminophosphate (SAPO), a chabazite, an erionite, and mixtures thereof, preferably, but not limited to, a SAPO catalyst. In the present invention, small pore molecular sieves are defined as having a pore size of less than about 5.0 Angstrom units. Generally, suitable catalysts have a pore size ranging from about 3.5 to about 5.0 Angstroms, preferably from about 4.0 to about 5.0 Angstroms, and most preferably from about 4.3 to about 5.0 Angstroms.

Zeolite materials, both natural and synthetic, have been demonstrated to have catalytic properties for various types of hydrocarbon conversion processes. In addition, zeolite materials have been used as adsorbents, catalyst carriers for various types of hydrocarbon conversion processes, and other applications. Zeolites are complex crystalline aluminosilicates which form a network of $AlO^-_2$ and $SiO_2$ tetrahedra linked by shared oxygen atoms. The negativity of the tetrahedra is balanced by the inclusion of cations such as alkali or alkaline earth metal ions. In the manufacture of some zeolites, non-metallic cations, such as tetramethylammonium (TMA) or tetrapropylammonium (TPA), are present during synthesis. The interstitial spaces or channels formed by the crystalline network enable zeolites to be used as molecular sieves in separation processes, as catalyst for chemical reactions, and as catalyst carriers in a wide variety of hydrocarbon conversion processes.

Zeolites include materials containing silica and optionally alumina, and materials in which the silica and alumina portions have been replaced in whole or in part with other oxides. For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

SAPO's have a three-dimensional microporous crystal framework structure of $PO_2^+$, $AlO_2^-$, and $SiO_2$ tetrahedral units. The chemical composition (anhydrous) is:

$$mR:(Si_xAl_yP_z)O_2$$

wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular SAPO species involved, and "x", "y", and "z" represent the mole fractions of silicon, aluminum and phosphorus, respectively. Typical small pore SAPO's are SAPO-17, SAPO-18, SAPO-34, SAPO-44, and others. "R" may be removed at elevated temperatures.

The metal which may be employed in the incorporation process is a transition metal selected from Groups VIB, VIIB, or VIII or mixtures thereof, as defined by the CAS Version of the CRC Handbook of Chemistry and Physics, 74th edition, 1993. Preferably, the metal is either nickel or cobalt.

The metal containing compounds which may be used in the present invention may be of various compositions, i.e. in the form of the corresponding halide, sulfate, acetate, carbonyl, nitrate, or mixtures thereof. When the desired catalyst comprises SAPO-34 and the metal is nickel, it is preferable to use the hydrated form of nickel acetate as the metal containing compound.

The process of incorporating the transition metal may be accomplished through any one of the standard methods well known to those skilled in the art. In one embodiment, a solution of the desired metal is first made by dissolving the desired amount of the metal containing compound in water under mild conditions. Preferably the water is de-ionized. The temperature of mixing is dependent upon the solubility of the metal compound in water, or whatever other medium is selected.

The process may be conducted under pressure or at atmospheric pressure.

After adequate mixing, the solution is then added to the selected amount of the molecular sieve. The resulting mixture is stirred as required. In some cases, stirring is not required and the mixture may be left undisturbed for a time adequate to permit the desired level of metal incorporation. The catalyst product is then filtered, optionally washed, dried, and calcined by methods well known to those skilled in the art.

The amount of metal which is incorporated onto the molecular sieve may vary over a wide range depending, at least in part, on the selected molecular sieve catalyst and on the incorporation method. The amount of metal incorporated is measured on an atomic metal basis in terms of silicon to metal ratio. The silicon to metal atomic ratios are in the range from about 0.01:1 to about 1000:1, preferably from about 0.1:1 to about 500:1, and most preferably from about 5:1 to about 50:1.

The conversion process employs a starting material (feedstock) comprising "oxygenates". As used herein, the term "oxygenates" is intended to comprise aliphatic alcohols, ethers, carbonyl compounds (aldehydes, ketones, carboxylic acids, carbonates, and the like) along with those compounds containing hetero-atoms, e.g., halides, mercaptans, sulfides, amines, and mixtures thereof. The aliphatic moiety preferably contains from about 1 to about 10 carbon atoms and more preferably contains from about 1 to about 10 carbon atoms. Representative oxygenates include, but are not limited to, lower straight or branched chain aliphatic alcohols, their unsaturated counterparts and the nitrogen, halogen and sulfur analogues of such. Examples of suitable compounds include, but are not limited to: methanol; ethanol; n-propanol; isopropanol; $C_4$–$C_{20}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, and n-alkyl halides, n-alkyl sulfides, each having n-alkyl groups of 3 to 10 carbon atoms; and mixtures thereof. The term "oxygenate" as employed herein designates only the organic material used as the feed. The total charge of feed to the reaction zone may contain additional compounds such as diluents.

The conversion process is preferably carried out in the vapor phase such that the feedstock is contacted with the defined molecular sieve catalyst at effective process conditions in a vapor phase in a reaction zone so as to produce the desired olefins. Effective process conditions include, but are not necessarily limited to an effective temperature, pressure, WHSV (Weight Hourly Space Velocity) and, optionally, an effective amount of diluent, correlated to produce olefins. Alternatively, the process may be carried out in a liquid phase. When the process is carried out in the liquid phase, different conversions and selectivities of feedstock-to-product may result with respect to the relative ratios of the light olefin products as compared to those formed by the vapor phase process.

The temperature which may be employed in the conversion process may vary over a wide range depending, at least in part, on the selected molecular sieve catalyst. The process is conducted at an effective temperature range from about 200° C. to about 700° C., preferably from about 250° C. to about 600° C., and most preferably from about 300° C. to about 500° C. Temperatures outside the stated preferred ranges are not excluded, although they do not fall within certain desirable embodiments of the present invention. At the lower end of the temperature range, and thus, generally, at a lower rate of reaction, the formation of the desired light olefin products may become markedly slow. At the upper end of the temperature range and beyond, the process may not form an optimum amount of light olefin products.

The process is effectively carried out over a wide range of pressures including autogeneous pressures. At pressures in the range from about 0.1 kPa to about 100 MPa, the formation of light olefin products will be effected although the optimum amount of product will not necessarily form at all pressures. The preferred pressure is in the range from about 6.9 kPa to about 34 Mpa, with the most preferred range being from about 48 kPa to about 0.34 MPa. The pressures referred to herein for the process are exclusive of the inert diluent, if any, that is present, and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range, and beyond, the selectivities, conversions and /or rates of convasion to light olefin products may not occur at the optimum, although light olefins such as ethylene may still be formed.

The process is effected for a period of time sufficient to produce the desired olefin products. In general, the residence time employed to produce the desired product can vary from seconds to a number of hours. It will be readily appreciated that the residence time will be determined to a significant extent by the reaction temperature, the pressure, the molecular sieve selected, the WHSV, the phase (liquid or vapor), and the process design characteristics selected.

The process is effectively carried out over a wide range of WHSV for the feedstock and is generally in the range from about 0.01 $hr^{-1}$ to about 500 $hr^{-1}$, preferably from about 0.1 $hr^{-1}$ to about 200 $hr^{-1}$, and most preferably from about 0.5 $hr^{-1}$ and 100 $hr^{-1}$. As the catalyst may contain other materials which act as inerts, the WHSV is calculated on the weight basis of methanol and small pore molecular sieve used.

The conversion process may optionally be carried out in the presence of one or more inert diluents which may be present in the feedstock for example in an amount between 1 and 99 molar percent, based on the total number of moles of all feed and diluent components fed to the reaction zone (or catalyst). Typical of diluents which may be employed in the instant process are helium, argon, nitrogen, carbon monoxide, carbon dioxide, hydrogen, water, paraffins, hydrocarbons (such as methane), aromatic compounds, and mixtures thereof. The preferred diluents are water and nitrogen.

The olefin production process may be carried out in a batch, semi-continuous or continuous fashion. The process can be conducted in a single reaction zone or a number of reaction zones arranged in series or in parallel, or may be conducted intermittently or continuously in an elongated tubular zone or in a number of such zones. When multiple reaction zones are employed, it may be advantageous to employ one or more of the defined small pore molecular sieves in series to provide for a desired product mixture.

Owing to the nature of the process, it may be desirous to carry out the process of the present invention using the molecular sieve catalysts in a dynamic bed system or any system of a variety of transport beds rather than in a fixed bed system. Such systems would readily provide for any regeneration (if required) of the molecular sieve catalyst after a given period of time. If regeneration is required, the molecular sieve catalyst can be continuously introduced as a moving bed to a regeneration zone where it can be regenerated, such as for example by removing carbonaceous materials or by oxidation in an oxygen-containing atmosphere. In the preferred practice of the invention, the catalyst will be subject to a regeneration step by burning off carbonaceous deposits accumulated during the conversion reactions.

The following examples illustrate, but do not limit, the present invention.

EXAMPLES

Catalysts were prepared and then tested for methanol conversion.

SAPO-34 was prepared according to U.S. Pat. No. 4,440,871 to provide a basis for comparision with the examples of transition metal incorporated small pore molecular sieve catalsyts as prepared by the methods as described above.

Example I

Ni-SAPO-34, was prepared as follows. A nickel containing solution was prepared by dissolving 0.26 g of $Ni(OAc)_2 \cdot 4H_2O$ in 23 cc of de-ionized water at room temperature. This solution was added to 3.92 grams of SAPO-34 and the mixture was stirred at room temperature for two hours. The finished catalyst was filtered, and then dried at 110° C. for 4 hours.

The resulting dried catalyst was then calcined at 550° C. for 16 hours. The silicon to nickel atomic ratio measured in terms of an atomic weight basis was about 1:10.

Example II

Co-SAPO-34, was prepared as follows. A cobalt containing solution was prepared by dissolving 0.25 g of $Co(OAc)_2 \cdot 4H_2O$ in 25 cc of de-ionized water at room temperature. This solution was added to 3.50 grams of SAPO-34 and the mixture was left to stand at room temperature overnight. The catalyst was filtered, and washed with 25 cc de-ionized water twice. The finished catalyst was dried at 110° C. for 4 hours. The resulting dried catalyst was then calcined at 520° C. for 16 hours. The silicon to cobalt atomic ratio was about 1:10.

Each of the prepared catalysts, the comparative and the two metal treated catalysts, was then tested using the following procedure. 5.0 cc (approximately 2.7 grams) of the selected SAPO-34 catalyst, were mixed with 15 cc of quartz beads and loaded into a ¾ outer diameter 316 stainless steel tubular reactor which was heated by a three-zone electric furnace. The first zone, acting as the preheating zone, vaporized the feed. The temperature of the center zone of the furnace was adjusted to give the desired reaction temperature of 450° C. The reactor was purged first with nitrogen at 50 cc/min flow rate for 30 minutes. The feed, a 4:1 (molar ratio) of water and methanol, was pumped into the reactor and calibrated to give a flow rate of about 0.7 hr$^{-1}$ WHSV. The effluent was analyzed at pre-determined intervals by an on-line gas chromatograph fitted with both a thermal conductivity detector and a flame ionization detector.

The results are shown in the following table.

| Olefins Yield | Comparative SAPO-34 | Invention Ni-SAPO-34 | Invention Co-SAPO-34 |
|---|---|---|---|
| Ethylene, wt. % | 49.2 | 65.5 | 52.6 |
| Propylene, wt. % | 34.0 | 24.8 | 33.6 |
| Total of $C_2^=$ and $C_3^=$, wt. % | 83.2 | 90.3 | 86.2 |

The examples illustrate an increase of over 30% in the ethylene yield using the Ni-SAPO-34 catalyst, as compared to the untreated SAPO-34 catalyst. The Co-SAPO-34 catalyst achieved a 7% increase in ethylene yield as compared to the untreated SAPO-34 catalyst. The combined ethylene and proplyene yield also increased by 8% and 3% respectively.

These results are comparable to those of Inui, which illustrated the positive effect that the presence of transition metals has on methanol conversion yields on SAPO catalysts. These improvements were effected with the more flexible catalyst preparation process of the present invention.

Thus, in the conversion of oxygenates to olefins, the use of a small pore molecular sieve with metal incorporated after synthesis is attractive. The present invention produces a similar catalyst which had the metal incorporated during synthesis, but avoids the commercially less attractive elevated temperature and elevated pressure metal incorporation process during synthesis.

What is claimed is:

1. A method for converting oxygenates to olefins comprising
   contacting said oxygenates with a small pore molecular sieve catalyst under production conditions effective to produce olefins;
   wherein said molecular sieve catalyst comprises a framework, and said framework is treated after synthesis with a transition metal compound comprising transition metal ions under catalyst treatment conditions effective to incorporate at least a portion of said transition metal ions onto said framework, wherein said transition metal ions are selected from the group consisting of Groups VIB, VIIB, or VIII and mixtures thereof.

2. The method of claim 1 wherein said molecular sieve catalyst is selected from the group consisting of a silicoaluminophosphate (SAPO), ZSM-34, chabazite, erionite, and mixtures thereof.

3. The method of claim 2 wherein said silicoaluminophosphate is selected from the group consisting of SAPO-17, SAPO-18, SAPO-34, and SAPO-44.

4. The method of claim 1 wherein said molecular sieve catalyst comprises pores having a size greater than about 3.5 Angstroms and less than about 5.0 Angstroms.

5. A method for converting oxygenates to olefins comprising
   contacting said oxygenates with a small pore molecular sieve catalyst under production conditions effective to produce olefins,
   wherein said molecular sieve catalyst comprises a framework, and said framework is treated after synthesis with a transition metal compound comprising transition metal ions under catalyst treatment conditions effective to incorporate at least a portion of said transition metal ions onto said framework, wherein said transition metal ions are selected from the group consisting of nickel, cobalt, and mixtures thereof.

6. The method of claim 1 wherein said transition metal compound is selected from the group consisting of halides, sulfates, acetates, carbonyls, nitrates, and mixtures thereof.

7. The method of claim 1 wherein said method produces a modified molecular sieve comprising a silicon to metal atomic ratio in the range of from about 0.1:1 to about 1000:1.

8. The method of claim 1 wherein said production conditions comprise a temperature of from about 200° C. to about 600° C.

9. The process of claim 1 wherein said oygenates feed is selected from the group consisting of methanol, ethanol, n-propanol, isopropanol, $C_4$–$C_{20}$ alcohols, methyl ethyl ether, di-methyl ether, di-ethyl ether, di-isopropyl ether, di-methyl carbonate, carbonyl compounds, and mixtures thereof.

10. The method of claim 9 wherein said oygenates comprise methanol or dimethyl ether.

11. The process of claim 1 wherein said oygenates further comprise a diluent.

12. The method of claim 11 wherein the diluent is selected from said group consisting of water, nitrogen, hydrogen, paraffins, olefins, aromatics, and mixtures thereof.

13. The method of claim 12 wherein said diluent is selected from the group consisting of water and nitrogen.

14. The method of claim 1 wherein said oxygenates are selected from the group consisting of a halide, a mercaptan, a sulfide, and an amine.

15. The method of claim 1 wherein said production conditions comprise a pressure of from about 0.1 kPa to about 100 MPa.

16. The method of claim 1 wherein said production conditions comprise a weight hourly space velocity in the range of from about 0.01 to about 500 hr$^{-1}$.

17. A method for converting oxygenates to olefins comprising:
   contacting said oxygenates with a molecular sieve catalyst selected from the group consisting of a SAPO, ZSM-34, a chabazite, an erionite, and mixtures thereof, under production conditions effective to produce olefins;
   wherein said molecular sieve catalyst comprises a framework comprising pores having a size less than about 5.0 Angstroms; and
   wherein said framework is treated after synthesis with a transition metal compound comprising transition metal ions selected from the group consisting of nickel, cobalt, and mixtures thereof, under catalyst treatment conditions effective to incorporate at least a portion of said transition metal ions onto said framework.

* * * * *